United States Patent
Milstein

(10) Patent No.: US 9,408,786 B2
(45) Date of Patent: Aug. 9, 2016

(54) METHOD FOR THE TREATMENT OF SKIN

(71) Applicant: Biopelle, Inc., Ferndale, MI (US)

(72) Inventor: Elliott Milstein, Ferndale, MI (US)

(73) Assignee: Biopelle, Inc., Ferndale, MI (US)

( * ) Notice: Subject to any disclaimer, the term of this patent is extended or adjusted under 35 U.S.C. 154(b) by 330 days.

(21) Appl. No.: 13/903,412

(22) Filed: May 28, 2013

(65) Prior Publication Data

US 2013/0259915 A1 Oct. 3, 2013

Related U.S. Application Data

(62) Division of application No. 12/582,499, filed on Oct. 20, 2009, now abandoned.

(60) Provisional application No. 61/111,819, filed on Nov. 6, 2008.

(51) Int. Cl.
*A61K 8/02* (2006.01)
*A61K 31/07* (2006.01)
*A61K 8/04* (2006.01)
*A61K 9/00* (2006.01)
*A61K 38/39* (2006.01)
*A61K 8/65* (2006.01)
*A61K 8/67* (2006.01)
*A61K 8/73* (2006.01)
*A61Q 19/00* (2006.01)
*A61K 47/42* (2006.01)

(52) U.S. Cl.
CPC . *A61K 8/044* (2013.01); *A61K 8/65* (2013.01); *A61K 8/671* (2013.01); *A61K 8/735* (2013.01); *A61K 9/0014* (2013.01); *A61K 31/07* (2013.01); *A61K 38/39* (2013.01); *A61Q 19/00* (2013.01); *A61K 47/42* (2013.01)

(58) Field of Classification Search
USPC .......................................... 424/401; 514/725
See application file for complete search history.

(56) References Cited

U.S. PATENT DOCUMENTS

| | | | |
|---|---|---|---|
| 5,002,760 A | 3/1991 | Katzev | |
| 5,153,174 A | 10/1992 | Band et al. | |
| 5,670,547 A * | 9/1997 | Milstein et al. | 514/725 |
| 5,744,148 A | 4/1998 | Habif et al. | |
| 7,189,406 B1 | 3/2007 | Gross | |
| 2003/0032601 A1* | 2/2003 | Kreuter et al. | 514/21 |
| 2003/0143288 A1 | 7/2003 | Mayne et al. | |
| 2003/0224060 A1 | 12/2003 | Simonnet et al. | |
| 2005/0244351 A1 | 11/2005 | Reinhart et al. | |
| 2006/0205679 A1 | 9/2006 | Streeper et al. | |
| 2007/0207112 A1* | 9/2007 | Gormley et al. | 424/70.14 |
| 2007/0280977 A1 | 12/2007 | Macian et al. | |
| 2008/0031907 A1 | 2/2008 | Tamarkin et al. | |
| 2008/0171031 A1 | 7/2008 | Jochim et al. | |
| 2009/0018102 A1 | 1/2009 | Moutet et al. | |

FOREIGN PATENT DOCUMENTS

| | | |
|---|---|---|
| EP | 1949887 A2 | 7/2008 |
| EP | 1992332 A1 | 11/2008 |
| WO | 0042989 A2 | 7/2000 |

OTHER PUBLICATIONS

Extended European Search Report for PCT/US2010/023724 dated Dec. 9, 2014, pp. 1-5.

* cited by examiner

*Primary Examiner* — Adam C Milligan
(74) *Attorney, Agent, or Firm* — Dinsmore & Shohl LLP; Weston R. Gould

(57) ABSTRACT

A composition for the treatment of skin comprises a non-emulsified, aqueous suspension of retinol. The composition may further include at least one protein species, and some proteins used in the composition include collagen and elastin. The composition may also include hyaluronic acid. The composition may also include one or more of tocopheryl acetate, propylene glycol, and linseed extract. Also disclosed are methods for making the composition and use of the composition for the treatment of skin.

4 Claims, No Drawings

METHOD FOR THE TREATMENT OF SKIN

CROSS-REFERENCE TO RELATED APPLICATIONS

This application is a divisional of U.S. patent application Ser. No. 12/582,499 filed Oct. 20, 2009, which in turn claims priority of U.S. Provisional Patent Application Ser. No. 61/111,819 filed Nov. 6, 2008, entitled "Retinol Formulations and Methods for Their Use", both of which are incorporated herein by reference.

FIELD OF THE INVENTION

This invention relates to formulations and methods for the treatment of skin. More particularly the invention relates to formulations and methods wherein the active ingredient is a retinol. Most specifically the invention relates to formulations and methods based upon non-emulsified compositions of retinol wherein retinol is suspended in an aqueous vehicle.

BACKGROUND OF THE INVENTION

Retinoic acid is a very effective agent for the treatment of a variety of skin conditions including, but not limited to, acne, photo aging, wrinkles, and the like. One particular retinoic acid material used for skin treatment is tretinoin (all-trans retinoic acid). While retinoic acid is a highly effective therapeutic material, it can cause a number of undesirable side effects which include skin irritation and skin thinning among others. As a consequence, topical formulations comprising retinoic acid must be used with caution, and dosage control is critical. In order to avoid adverse side effects, retinoic acid therapies often rely upon the use of topical preparations of retinoic acid precursors and derivatives.

Retinol is a member of the vitamin A family and can be converted to retinoic acid under oxidizing conditions. As is known in the art, when retinol is applied to the skin, it can bioconvert to retinoic acid, and this conversion reaction is fostered by the presence of proteins. For this reason, retinol based preparations are attractive for use as therapeutic agents for the treatment of a variety of skin conditions since they can act, controllably, to deliver retinoic acid to the skin. However, retinol is a fat-soluble material and has very low solubility in aqueous vehicles. This solubility problem has limited the use of retinol based formulations.

In some instances, in order to overcome the disadvantages of using an oil based therapeutic material, emulsified preparations of retinol have been prepared. As is understood in the art, an emulsified formulation comprises a microstructure having an oily phase disposed in a continuous, aqueous phase (oil in water emulsion) or an aqueous phase disposed in an oily, continuous phase (water in oil emulsion). In an emulsion, the first phase may be present in the form of discrete vesicles or in layered (lamellar) structures which are disposed in the continuous phases. In the context of this disclosure, all of such dual phase formulations are understood to be emulsions. A typical emulsion requires the presence of an emulsifying agent in order to prevent the phases from separating and thereby destroying the emulsion. The emulsifying agent comprises a molecule having an oleophilic portion which binds to the material comprising the oily phase and a hydrophilic portion which binds to the aqueous phase.

While emulsified preparations of retinol are known, it has been found that emulsified preparations of retinol have decreased efficacy when used as topical agents for the treatment of skin. This is because the emulsified structure inhibits the absorption of retinol by the skin and its subsequent bioconversion to the active, retinoic acid form. As a consequence, retinol based skin treatment formulations have been found to have limited utility, and hence the more risky retinoic acid based formulations are often used instead. As will be explained hereinbelow, the present invention provides aqueous-based, non-emulsified retinol preparations which are highly effective in treating various skin conditions.

BRIEF DESCRIPTION OF THE INVENTION

Disclosed is a composition for the treatment of skin, which comprises a non-emulsified, aqueous suspension of retinol. The composition may further include at least one protein species, and some proteins which may be employed in the invention include collagen and elastin. The composition may include further ingredients such as hyaluronic acid as well as adjunct agents including thickeners, fragrances, coloring agents, preservatives, and buffers.

Specific compositions include, on a weight basis, 0.1-5.0% retinol and 1-20% of at least one protein species, together with water and at least one dispersing agent which operates to suspend the retinol. The composition is characterized in that it is not an emulsion and the retinol is suspended in the water. In specific instances, the retinol is in the form of a plurality of droplets which have a size in the range of 5-500 microns.

Another specific composition comprises, on a weight basis, 0.1-5% retinol, 1-15% soluble collagen, 0.5-5% hydrolyzed elastin, 0.2-2% hyaluronic acid, 0.5-10% glycerin, one or more dispersing agents, and water. Also disclosed are other compositions as well as methods for preparing and using the compositions.

DETAILED DESCRIPTION OF THE INVENTION

The present invention recognizes that retinol can be a highly effective agent for the treatment of skin when it is applied thereto in a non-emulsified vehicle. Specifically, the present invention recognizes that retinol may be compounded into a suspension of fine droplets which are dispersed in an aqueous vehicle, and that this suspension will have enhanced utility as compared to emulsified preparations. This finding is counterintuitive and unexpected. Emulsified compositions are easy to prepare, and are considered in the art to be the optimum vehicle for delivering retinol to the skin. Suspensions are much more difficult to prepare than are emulsions. Furthermore, the prior art had no reason to expect that suspensions of retinol would be any more effective than emulsions as a topical treatment for skin. Hence, the prior art has never considered or employed suspensions of retinol for the treatment of skin conditions, and has not anticipated the enhanced therapeutic effect of the suspensions of the present invention.

In accord with the present invention it has been found that a composition for the treatment of skin comprising a non-emulsified, aqueous suspension of a retinol is highly effective in the topical treatment of a variety of skin conditions. In the art, the term "retinol" is used broadly to refer to a family of materials of the general formula $C_{20}H_{30}O$ having a terminal hydroxyl group. The term "retinol" also is used to refer to esters and other derivatives of this alcohol since these materials are often found in the biological systems as precursors of retinol. In the context of this disclosure, the term "retinol" is understood to include all of such materials.

The materials of the present invention are specifically characterized in that the compositions do not comprise any type of emulsified structure. As such, they do not include any material which is operative, in the formulation, to bind to an oily phase material and to an aqueous phase material so as to form a vesicular or lamellar emulsion structure. It is to be understood that compositions of the present invention may include materials which can function as emulsifiers in other systems, provided that those materials are not operative in the present formulations to form or sustain any emulsion. The compositions of the present invention can include dispersants or other suspension promoting agents which, through electrostatic action, rheological control, or some other mechanism, maintain the retinol in suspension. As detailed above, the suspensions of the present invention are differentiated from emulsions by the lack of an emulsifying agent which binds to the retinol and to the aqueous phase. This distinction is significant since it is believed to be responsible for the fact that the suspensions of the present invention have a greater therapeutic effect than do comparable emulsified preparations.

The compositions of the present invention may further include other performance ingredients. In one particular group of instances, the formulations include one or more proteins therein, and it has been found that inclusion of a protein can enhance the bioconversion of the retinol to retinoic acid. Typically, the proteins are present in a solubilized form. Some of the proteins which may be included in the formulations of the present invention include soluble collagen and hydrolyzed elastin. The compositions may also include other performance ingredients such as hyaluronic acid. The compositions may also include ancillary ingredients as is known in the art and these may include thickeners, fragrances, coloring agents, preservatives, buffers, and the like.

The amount of retinol present in the composition will depend upon particular applications. In some instances, it has been found that the concentration of the retinol will be in the range of 0.1-5.0%. This concentration is given on the basis of weight, and unless otherwise noted, all concentrations given herein are on a weight/weight basis. In those instances where proteins are incorporated, they will typically be present in an amount of 1-20%; although, higher or lower concentrations are also contemplated. Hyaluronic acid, when it is included, is typically present in a concentration of 0.1-5%.

One particular group of compositions of the present invention may be formulated as an aqueous dispersion which includes at least the following performance materials:
0.1-5% retinol;
1-15% soluble collagen;
0.5-5% hydrolyzed elastin;
0.2-2% hyaluronic acid; and
0.5-10% glycerin.

The foregoing composition may also include additional agents, and in one particular group of instances, the composition further includes:
0.5-5% propylene glycol;
0.1-2% tocopheryl acetate;
0.5-5% Linum usitatissimum (linseed) seed extract;
0.5-5% magnesium aluminum silicate;
0.1-3% octoxynol-9;
0.1-2% quaternium-15;
0.1-5% polysorbate 20; and
0.1-2% xanthan gum.

One particular composition of the present invention comprises:
magnesium aluminum silicate 0.99%;
soluble collagen 8.00%;
hydrolyzed elastin 2.00%;
hyaluronic acid 1.00%;
Linum usitatissimum (linseed) seed extract 0.98%;
retinol 1.00%;
tocopheryl acetate 0.50%;
octoxynol-9 0.80%;
quaternium-15 0.30%;
propylene glycol 0.90%;
glycerin 3.00%;
polysorbate 20 1.00%;
xanthan gum 0.50%; and
balance water.

In another group of formulations, the retinol component is employed in the form of a pre-blended, 50/50 mixture of retinol and polysorbate 20. This is for convenience and it is to be understood that the pre-blended mixture need not be employed. One formulation of this type comprises:
magnesium aluminum silicate 0.99%;
soluble collagen 8.00%;
hydrolyzed elastin 2.00%;
sodium hyaluronate 1.00%;
Linum usitatissimum (linseed) seed extract 0.98%;
retinol/polysorbate (50/50 mixture) 1.00%;
tocopheryl acetate 0.50%;
octoxynol-9 0.80%;
quaternium-15 0.30%;
propylene glycol 0.90%;
glycerin 3.00%;
xanthan gum 0.50%;
Yellow No. 5 (1% solution) 0.12%; and
water balance.

A second formulation of this type comprises:
magnesium aluminum silicate 0.99%;
soluble collagen 8.00%;
hydrolyzed elastin 2.00%;
sodium hyaluronate 1.00%;
Linum usitatissimum (linseed) seed extract 0.98%;
retinol/polysorbate (50/50 mixture) 2.00%;
tocopheryl acetate 0.50%;
octoxynol-9 0.80%;
polysorbate 20 2.50%;
quaternium-15 0.30%;
propylene glycol 0.90%;
glycerin 3.00%;
xanthan gum 0.50%;
Yellow No. 5 (1% solution) 0.22%; and
water balance.

The foregoing formulations may be readily prepared by dispersing liquid retinol and the other components into the aqueous vehicle. Dispersion may be facilitated by the use of a blender, mill, or the like. In some instances, the particle or droplet size of the retinol is in the range of 5 microns-500 microns; although, other sizes may be utilized in particular formulations.

In a typical therapeutic protocol, the composition is applied to the skin one or two times a day; although other application schedules may be employed in particular instances.

The foregoing is descriptive of some particular embodiments and implementations of the present invention and is meant to be illustrative of the general principles thereof, and not a limitation upon the practice of the invention. Other modifications and variations will be readily apparent to those of skill in the art in view of the teaching presented herein. It is the following claims, including all equivalents, which define the scope of the invention.

The invention claimed is:
1. A method for the treatment of skin, said method comprising applying to the skin a non-emulsified composition comprising, on a weight basis:
0.99% magnesium aluminum silicate;

8.00% soluble collagen;
2.00% hydrolyzed elastin;
1.00% sodium hyaluronate;
0.98% Linum usitatissimum (linseed) seed extract;
1.00% retinol/polysorbate 20 (50/50 mixture);
0.50% tocopheryl acetate;
0.80% octoxynol-9;
0.30% quaternium-15;
0.90% propylene glycol;
3.00% glycerin;
0.50% xanthan gum; and
water.

2. The method of claim 1, wherein said composition further includes, on a weight basis, at least one or more ancillary agent selected from the group consisting of: coloring agents, fragrances, thickening agents, buffers, and preservatives.

3. A method for the treatment of skin, said method comprising applying to the skin a non-emulsified composition comprising, on a weight basis:

0.99% magnesium aluminum silicate;
8.00% soluble collagen;
2.00% hydrolyzed elastin;
1.00% sodium hyaluronate;
0.98% Linum usitatissimum (linseed) seed extract;
2.00% retinol/polysorbate 20 (50/50 mixture);
0.50% tocopheryl acetate;
0.80% octoxynol-9;
2.50% polysorbate 20;
0.30% quaternium-15;
0.90% propylene glycol;
3.00% glycerin;
0.50% xanthan gum; and
water.

4. The method of claim 3, wherein said composition further includes, on a weight basis, at least one or more ancillary agent selected from the group consisting of coloring agents, fragrances, thickening agents, buffers, and preservatives.

* * * * *